United States Patent [19]

Morton, Jr.

[11] 4,069,389

[45] Jan. 17, 1978

[54] 3,7-INTER-M-PHENYLENE-4,5,6-TRINOR-9-DEOXY-9,10-DIDEHYDRO-PGD$_1$ COMPOUNDS

[75] Inventor: Douglas Ross Morton, Jr., Portage, Mich.

[73] Assignee: The Upjohn Company, Kalamazoo, Mich.

[21] Appl. No.: 756,110

[22] Filed: Dec. 30, 1976

Related U.S. Application Data

[62] Division of Ser. No. 614,242, Sept. 17, 1975, Pat. No. 4,016,184.

[51] Int. Cl.$^2$ .............................................. C07C 69/76
[52] U.S. Cl. ................................... 560/53; 260/520 B; 260/520 C; 560/51
[58] Field of Search ........... 260/473 R, 473 G, 520 C, 260/520 B, 520 R

[56] References Cited

FOREIGN PATENT DOCUMENTS

| 30,848 | 7/1973 | Japan ................................ 260/473 R |
| 7,301,094 | 7/1973 | Netherlands ..................... 260/473 R |

Primary Examiner—Paul J. Killos
Attorney, Agent, or Firm—Robert A. Armitage

[57] ABSTRACT

Prostaglandin analogs with the following cyclopentane ring structure:

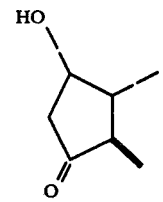

,

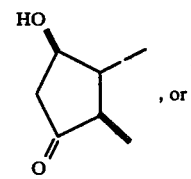

, or

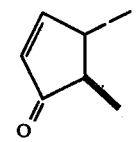

are disclosed along with intermediates useful in their preparation and processes for their preparation. These analogs are useful for the same pharmacological purposes as the prostaglandins, particularly and especially as blood platelet aggregation inhibitors.

33 Claims, No Drawings

3,7-INTER-M-PHENYLENE-4,5,6-TRINOR-9-DEOXY-9,10-DIDEHYDRO-PGD₁ COMPOUNDS

The present application is a divisional application of Ser. No. 614,242, filed Sept. 17, 1975, now issued as U.S. Pat. No. 4,016,184, on Apr. 5, 1977.

The present invention relates to prostaglandin analogs for which the essential material constituting a disclosure therefor is incorporated by reference here from U.S. Pat. No. 4,016,184, issued Apr. 5, 1977.

I claim:

1. A prostaglandin analog of the formula

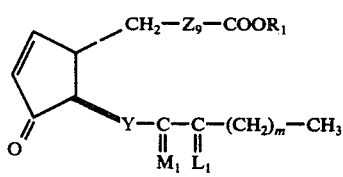

wherein Y is cis-CH=CH— or trans -CH=CH—;
wherein m is one to 5, inclusive;
wherein M₁ is

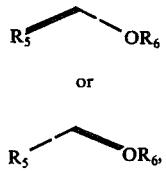

or

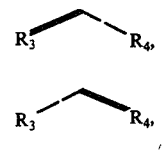

wherein $R_5$ and $R_6$ are hydrogen or methyl, with the proviso that one of $R_5$ and $R_6$ is mehtyl only when the other is hydrogen;
wherein L₁ is

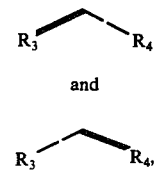

or a mixture of $R_3 \quad R_4$, and $R_3 \quad R_4$, wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen, alkyl of one ot 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically accepted cation; and
wherein Z₉ is

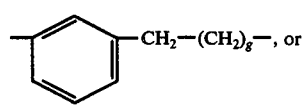

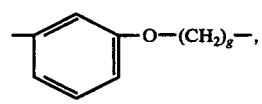

wherein g is one, 2, or 3.

2. A compound according to claim 1, wherein M₁ is

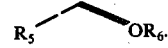

3. A compound according to claim 1, wherein M₁ is

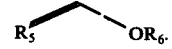

4. A compound according to claim 3, wherein Y is cis-CH=CH—.

5. A compound according to claim 4, wherein m is 3.

6. A compound according to claim 5, wherein g is 3.

7. 2a,2b -Dihomo-3,7-inter-m-phenylene-4,5,6-trinor-9- 9,10-didehydro-15-epi-cis-13-PGD₁, a compound according to claim 6.

8. A compound according to claim 5, wherein g is one.

9. 3,7-Inter-m-phenylene-4,5,6-trinor-9-deoxy-9,10-didehydro-15-epi-cis-13-PGD₁, a compound according to claim 8.

10. 3,7-Inter-m-phenylene-4,5,6-trinor-3-oxa-9-deoxy-9,10-didehydro-15-epi-cis-13PGD₁a compound according to claim 8.

11. A compound according to claim 3, wherein Y is trans-CH=CH—.

12. A compound according to claim 11, wherein m is 3.

13. A compound according to claim 12, wherein Z₉ is

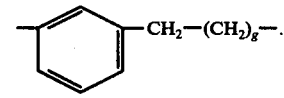

14. A compound according to claim 13, wherein g is 3.

15. A compound according to claim 13, wherein g is one.

16. A compound according to claim 15, wherein $R_5$ and $R_6$ are both hydrogen.

17. A compound according to claim 16, wherein $R_3$ and $R_4$ are both hydrogen.

18. 3,7-inter-m-phenylene-4,5,6-trinor-9-deoxy-9,10-dide-hydro-PGD₁, a compound according to claim 17.

19. A compound according to claim 16, wherein $R_3$ and $R_4$ are both fluoro.

20. 16,16-Difluoro-3,7-inter-m-phenylene-4,5,6-trinor-8-deoxy-9,10-didehydro-PGH₁, a compound according to claim 19.

21. A compound according to claim 13, wherein Z₉ is

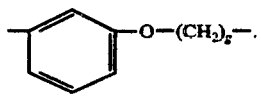

22. A compound according to claim 21, wherein g is 3.

23. A compound according to claim 22, wherein $R_5$ and $R_8$ are both hydrogen.

24. A compound according to claim 23, wherein $R_3$ and $R_4$ are both hydrogen.

25. 2a,2b-Dihomo-3,7-inter-m-phenylene-4,5,6-trinor-3-oxa9-deoxy-9,10-didehydro-PGD$_1$, a compound according to claim 24.

26. A compound according to claim 23, wherein $R_3$ and $R_4$ are both fluoro.

27. 2a,2b-Dihomo-16,16-difluoro3,7-inter-m-phenylene-4,5,6-trinor-3-oxa-9-deoxy-9,10-didehydro-PGD$_1$, a compound according to claim 26.

28. A compound according to claim 21, wherein g is one.

29. A compound according to claim 28, wherein $R_5$ and $R_6$ are both hydrogen.

30. A compound according to claim 30, wherein $R_3$ and $R_4$ are both hydrogen.

31. 3,7-Inter-m-phenylene-4,5,6-trinor-3-oxa-9-deoxy9,10-didehydro-PGD$_1$, a compound according to claim 30.

32. A compound according to claim 29, wherein $R_3$ and $R_4$ are both fluoro.

33. 16,16-Difluoro-3,7-inter-m-phenylene-4,5,6-trinor-3-oxa-9-deoxy-9,10-didehydro-PGH$_1$, a compound according to claim 32.

UNITED STATES PATENT OFFICE
CERTIFICATE OF CORRECTION

Patent No. 4,069,389                             Dated January 17, 1978

Inventor(s)   D. R. Morton, Jr.

It is certified that error appears in the above-identified patent and that said Letters Patent are hereby corrected as shown below:

Column 2, line 30, '9- 9,10-didehydro" should read -- 9-deoxy-9,10-didehydro --; line 61, "dide-hydro" should read -- didehydro --; line 65, "8-deoxy-9,10-didehydro-$PGH_1$," should read -- 9-deoxy-9,10-didehydro-$PGD_1$,--; line 38, "cis-13$PGD_1$a compound" should read -- cis-13-$PGD_1$, a compound --.

Column 3, line 11, "and $R_8$" should read -- and $R_6$ --; line 15, "3-oxa9-deoxy" should read -- 3-oxa-9-deoxy --.

Column 4, line 1, "difluoro3,7-" should read -- difluoro-3,7- --; line 8, "according to claim 30" should read -- according to claim 29 --; line 16, "$PGH_1$," should read -- $PGD_1$ --.

Signed and Sealed this

Sixth Day of June 1978

[SEAL]

Attest:

RUTH C. MASON
*Attesting Officer*

DONALD W. BANNER
*Commissioner of Patents and Trademarks*